(12) United States Patent
Moberg et al.

(10) Patent No.: US 9,039,751 B2
(45) Date of Patent: May 26, 2015

(54) ENDOPROSTHESIS DELIVERY SYSTEM

(75) Inventors: John R. Moberg, Elk River, MN (US);
Michael Gerdts, Big Lake, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 979 days.

(21) Appl. No.: 12/691,637

(22) Filed: Jan. 21, 2010

(65) Prior Publication Data
US 2010/0121427 A1 May 13, 2010

Related U.S. Application Data

(62) Division of application No. 10/961,804, filed on Oct. 8, 2004, now Pat. No. 7,658,757.

(51) Int. Cl.
*A61F 2/06* (2013.01)
*A61F 2/95* (2013.01)

(52) U.S. Cl.
CPC ............ *A61F 2/95* (2013.01); *A61F 2002/9517* (2013.01)

(58) Field of Classification Search
CPC ... A61F 2/95; A61F 2002/9517; A61F 2/962; A61B 2019/2246
USPC ......................... 623/1.11, 1.12, 1.23; 606/108
See application file for complete search history.

(56) References Cited

U.S. PATENT DOCUMENTS

| | | | |
|---|---|---|---|
| 4,530,855 A | 7/1985 | Youngkeit | |
| 4,861,621 A | 8/1989 | Kanzaki | |
| 4,862,922 A | 9/1989 | Kite | |
| 5,335,167 A | 8/1994 | Boyd | |
| 5,571,168 A | 11/1996 | Toro | |
| 5,601,599 A | 2/1997 | Nunez | |
| 5,607,531 A | 3/1997 | Needham et al. | |
| 5,614,139 A | 3/1997 | Cutolo | |
| 5,733,267 A | 3/1998 | Del Toro | |
| 5,788,707 A | 8/1998 | Del Toro et al. | |
| 5,957,930 A | 9/1999 | Vrba | |
| 5,980,533 A | 11/1999 | Holman | |
| 6,042,588 A | 3/2000 | Munsinger | |
| 6,068,634 A | 5/2000 | Lorentzen | |
| 6,096,045 A | 8/2000 | Del Toro et al. | |
| 6,342,066 B1 | 1/2002 | Toro et al. | |

(Continued)

OTHER PUBLICATIONS

Schetsky, L. McDonald, "Shape Memory Alloys", Encyclopedia of Chemical Technology (3rd ed.), John Wiley & Sons, 1982, 01.20, pp. 726-736.

*Primary Examiner* — Katherine Dowe
(74) *Attorney, Agent, or Firm* — Seager, Tufte & Wickhem, LLC

(57) ABSTRACT

Endoprothesis delivery systems and methods for making an using the same. An example medical endoprosthesis delivery system may include an inner member. An outer member may at least partially surround the inner member. The inner member and the outer member may be configured so that an implantable medical endoprosthesis can be disposed therebetween. A coupling device may be coupled to a portion of the outer member so that, when there is substantially no slack in the coupling device, as the coupling device moves in a proximal direction the portion of the outer member moves in the proximal direction. An adjustable stop may be coupled to the coupling device so that, when there is slack in the coupling device, as the adjustable stop is moved in the proximal direction, the amount of slack in the coupling device can be reduced.

17 Claims, 3 Drawing Sheets

(56) References Cited

U.S. PATENT DOCUMENTS

| | | |
|---|---|---|
| 6,395,017 B1 | 5/2002 | Dwyer |
| 6,425,898 B1 | 7/2002 | Wilson et al. |
| 6,468,298 B1 | 10/2002 | Pelton |
| 6,508,825 B1 | 1/2003 | Selmon et al. |
| 6,602,226 B1 | 8/2003 | Smith et al. |
| 6,605,107 B1 | 8/2003 | Klein |
| 6,605,109 B2 | 8/2003 | Fiedler |
| 6,610,069 B2 | 8/2003 | Euteneuer et al. |
| 6,613,072 B2 | 9/2003 | Lau et al. |
| 6,613,077 B2 | 9/2003 | Gilligan |
| 6,616,650 B1 | 9/2003 | Rowe |
| 6,620,191 B1 | 9/2003 | Svensson |
| 6,620,193 B1 | 9/2003 | Lau et al. |
| 6,623,491 B2 | 9/2003 | Thompson |
| 6,623,518 B2 | 9/2003 | Thompson et al. |
| 6,626,934 B2 | 9/2003 | Blaeser |
| 6,669,716 B1 | 12/2003 | Gilson et al. |
| 6,743,219 B1 | 6/2004 | Dwyer et al. |
| 6,773,446 B1 | 8/2004 | Dwyer et al. |
| 6,786,918 B1 | 9/2004 | Krivoruchko et al. |
| 2004/0002727 A1 | 1/2004 | Hwang |
| 2004/0097959 A1 | 5/2004 | Thompson |
| 2005/0038493 A1* | 2/2005 | Feeser .................. 623/1.11 |
| 2005/0070764 A1* | 3/2005 | Nobis et al. .................. 600/131 |

* cited by examiner

ENDOPROSTHESIS DELIVERY SYSTEM

CROSS-REFERENCE TO RELATED APPLICATIONS

This application is a divisional of U.S. application Ser. No. 10/961,804, filed Oct. 8, 2004, now U.S. Pat. No. 7,658,757, the entire disclosures of which is hereby incorporated by reference.

TECHNICAL FIELD

This invention relates to endoprosthesis delivery systems and related methods.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include an outer member surrounding an inner member with a stent positioned therebetween. Generally, the operator of the system positions the distal portion within the lumen at a desired location (e.g., so that the stent is adjacent an occlusion). The operator can then retract the outer member to allow the stent to engage the occlusion/lumen wall. Thereafter, the operator removes the distal portion of the system from the lumen.

SUMMARY

In general, the invention relates to endoprosthesis delivery systems and related methods. The systems can be used, for example, to deliver a medical endoprosthesis (e.g., a stent) at a desired location within a lumen of a subject (e.g., an artery of a human).

The systems generally include an inner member and an outer member at least partially surrounding the inner member. The inner member and the outer member are configured so that an implantable medical endoprosthesis (e.g., a stent) can be disposed therebetween. In general, the systems also include a device (e.g., a wire) that communicates with a portion of the outer member (e.g., a distal portion of the outer member) so that, when there is substantially no slack in the device, as the device moves in a proximal direction, the portion of the outer member that communicates with the device also moves in the proximal direction. The systems typically further include an adjustable stop that communicates with the device so that, when there is slack in the device, as the adjustable stop is moved in the proximal direction, the amount of slack in the device can be reduced.

In some embodiments, the adjustable stop includes a shaft that is coupled to the inner member, and a member that is moveable along the outer surface of the shaft in the proximal direction.

In certain embodiments, the adjustable stop includes a shaft that is coupled to the inner member, a first member and a second member. The shaft has a threaded surface, and the first member (e.g., a nut) is moveable in the proximal direction along the threads of the outer surface of the shaft. The second member is configured so that, as the first member moves in the proximal direction, the first member engages the second member.

In some embodiments, the implantable medical endoprosthesis delivery system can be designed to reduce (e.g., eliminate) slack in the device that is used to move the outer member in the proximal direction during deployment of the implantable medical endoprosthesis (e.g., stent). This can enhance the control available to the user (e.g., surgeon) during deployment of the implantable medical endoprosthesis. Alternatively or additionally, reducing (e.g., removing) slack in the device can allow for more precise placement of the implantable medical endoprosthesis at a desired location (e.g., within a lumen of a subject).

Other features and advantages of the invention will be apparent from the description, drawings and claims.

DESCRIPTION OF DRAWINGS

Like reference symbols in the various drawings indicate like elements.

DETAILED DESCRIPTION

Figure 1:
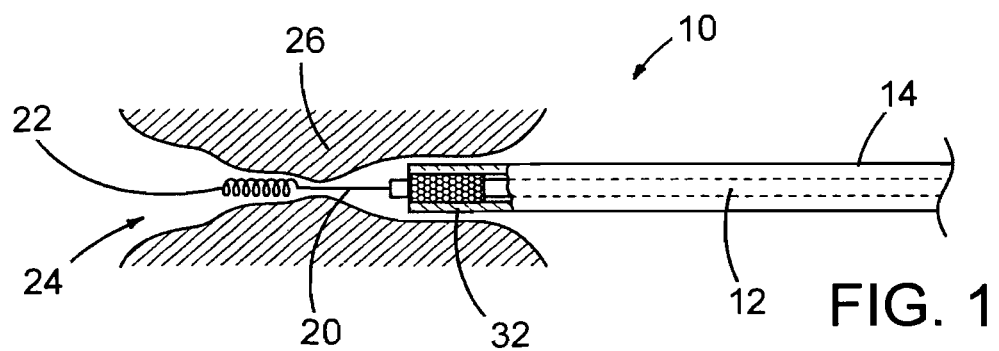
FIGS. 1-3 are side views of a distal portion of an implantable medical endoprosthesis delivery system during use.
Figure 2:
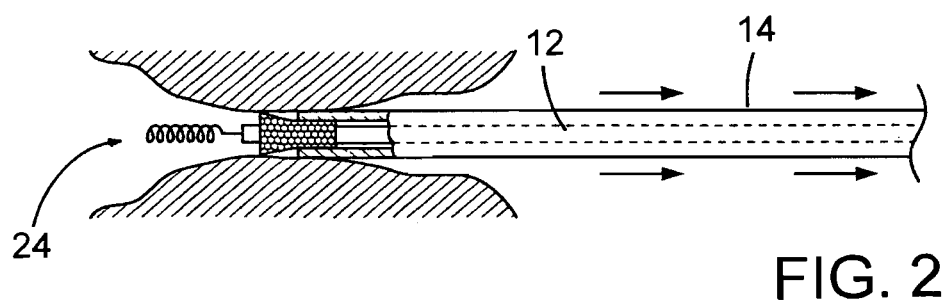
Figure 3:
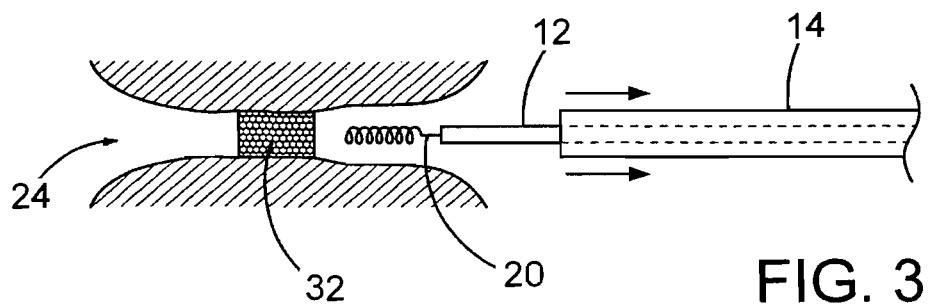

FIGS. 1-3 show a distal end of an implantable medical endoprosthesis delivery system 10 that includes an inner member 12, an outer member 14 surrounding inner member 12, and a stent 32 positioned between inner member 12 and outer member 14. The distal end of system 10 is dimensioned for insertion into a body lumen (e.g., an artery of a human). A guide wire 20 with a blunted end 22 is inserted into a body lumen 24 by, for example, making an incision in the femoral artery, and directing guide wire 20 to a constricted site 26 of lumen 24 (e.g., an artery constricted with plaque) using, for example, fluoroscopy as a position aid. After guide wire 20 has reached constricted site 26 of body lumen 24, inner member 12, stent 32 and outer member 14 are placed over the proximal end of guide wire 20. Inner member 12, stent 32 and outer member 14 are moved distally over guide wire 20 and positioned within lumen 24 so that stent 32 is adjacent constricted site 26 of lumen 24. Outer member 14 is moved proximally by pulling or retracting a pull wire (as will be further described below), allowing stent 32 to expand and engage constricted site 26. Outer member 14, inner member 12 and guide wire 20 are removed from body lumen 24, leaving stent 32 engaged with constricted site 26.

Figure 4A:
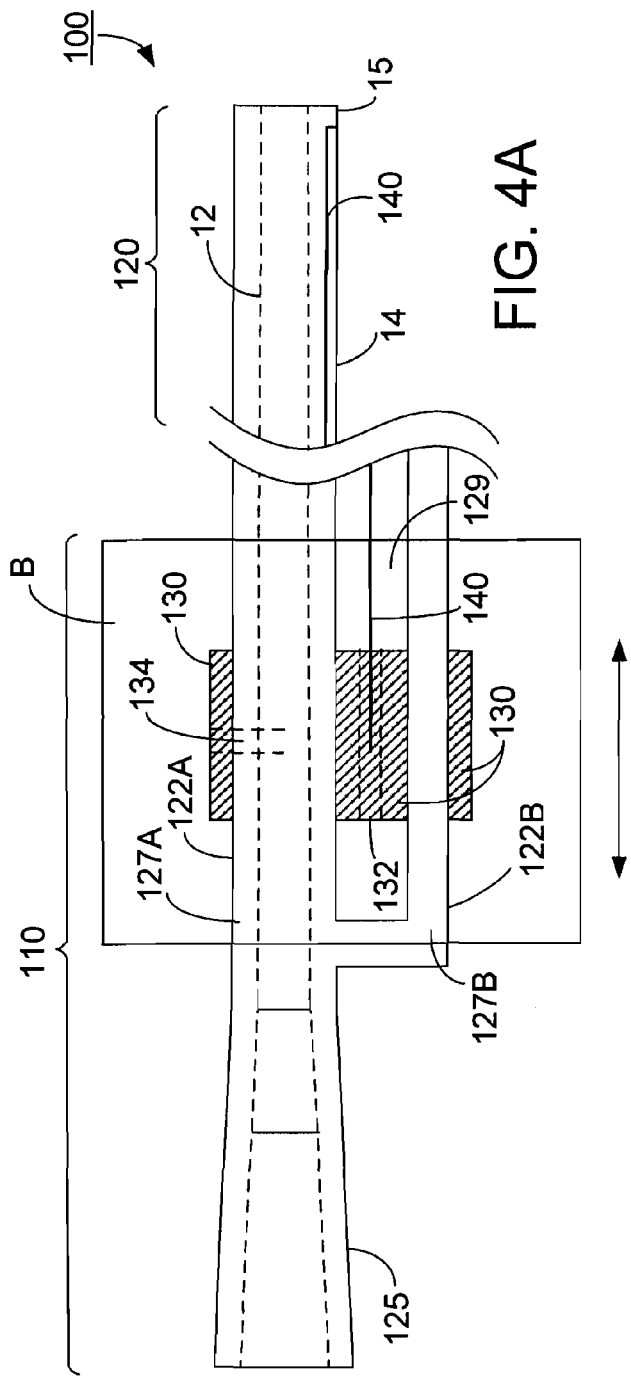
FIG. 4A is a cross sectional view of an implantable medical endoprosthesis delivery system.
Figure 4B:
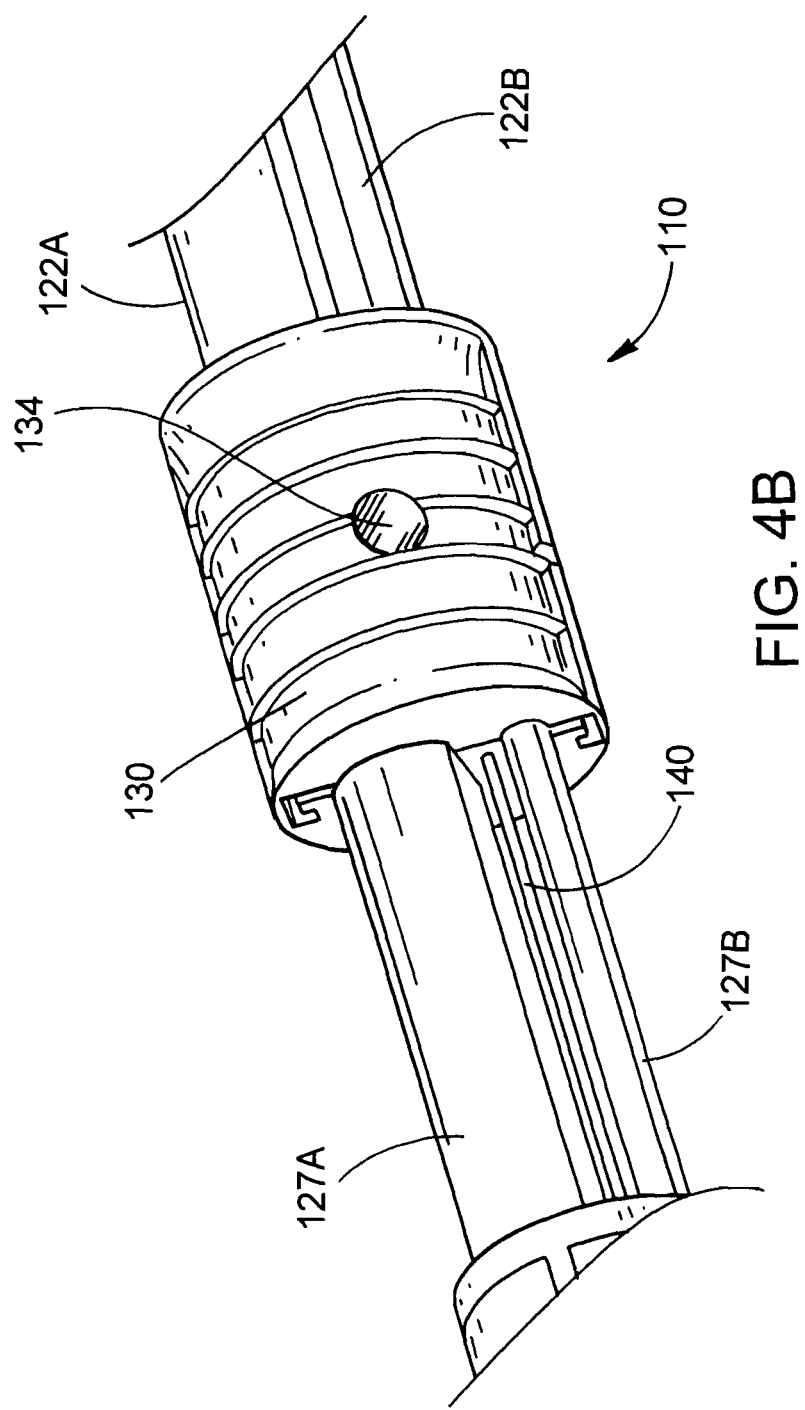
FIG. 4B is a perspective view of area B of the implantable medical endoprosthesis delivery system shown in FIG. 4A.

FIGS. 4A and 4B show an implantable medical endoprosthesis delivery system 100 including proximal and distal portions 110 and 120, respectively, that are connected to each other. Proximal portion 110 includes a handle 125 including shafts 127A and 127B and an opening 129 therebetween. Proximal portion 110 also includes a member 130 that can move an along outer surfaces 122A and 122B of shafts 127A and 127B, respectively (see arrow). Member 130 includes a groove 132 dimensioned so that a wire 140 can fit within groove 132. The opposite end of wire 140 is connected to a location 15 at a distal portion of outer member 14. Member 130 has a threaded orifice 134 configured so that a set screw (not shown) can be fit into orifice 134. With this arrangement, when the set screw is not present in orifice 134, wire 140 is not coupled to member 130. However, when the set screw is screwed into threaded orifice 134, the set screw can securely contact wire 140 so that wire 140 is coupled to member 130. Thus, when there is slack present in wire 140, the set screw can be positioned so that wire 140 is not coupled to member 130. The slack in wire 140 can be removed by pulling wire 140 in the proximal direction (e.g., using the operator's hands, using a pair of pliers) to position the proximal end of wire 140 further into groove 132 without moving member 130 until the slack in wire 140 is removed. After the slack in wire 140 is removed, the set screw can be sufficiently screwed into orifice 134 so that wire 140 is coupled to member 130. When wire 140 and member 130 are coupled, moving member 130 in the proximal direction over outer surfaces 122 A and 122B of shafts 127A and 127B, respectively, also moves wire 140 in the proximal direction, which, in turn, moves outer member 14 in the proximal direction, exposing stent 32 (not shown in FIGS. 4A and 4B) to expand to engage constricted site 26.

In some embodiments, member 130 is formed of a unitary piece of material (e.g., a plastic, such as a nylon, polyester, polyethylene or polypropylene). For example, member 130 can have a unitary clamshell configuration. In certain embodiments, member 130 is formed of multiple pieces of material (e.g., two pieces of material, three pieces of material, four pieces of material, five pieces of material). Member 130 can be formed, for example, by machining, injection molding, injection co-molding, casting, extrusion and/or co-extrusion. In some embodiments (e.g., when it is desired to enhance the ability of member 130 to slide along surfaces 122A and 122B of shafts 127A and 127B, respectively), the exposed surfaces of member 130 and/or shafts 127 A and 127B can be formed of a material having a relatively low coefficient of friction (e.g., a fluoropolymer or a silicone), and/or the exposed surfaces member 130 and/or shafts 127A and 127B can be made of a material (e.g., a plastic) that includes a lubricious additive (e.g., a fluoropolymer, a silicone, an ultrahigh molecular weight polyethylene, an oil, or blends thereof). Examples of fluoropolymers include PTFE and FEP.

In some embodiments, member 130 and shafts 127A and 127B are configured such that a certain minimum force is applied to member 130 before it can slide along outer surfaces 122A and 122B of shafts 127A and 127B, respectively. This can, for example, reduce the possibility of inadvertent movement of member 130 or wire 140. Alternatively or additionally, member 130 can include a trigger having a controlled release.

Figure 5:
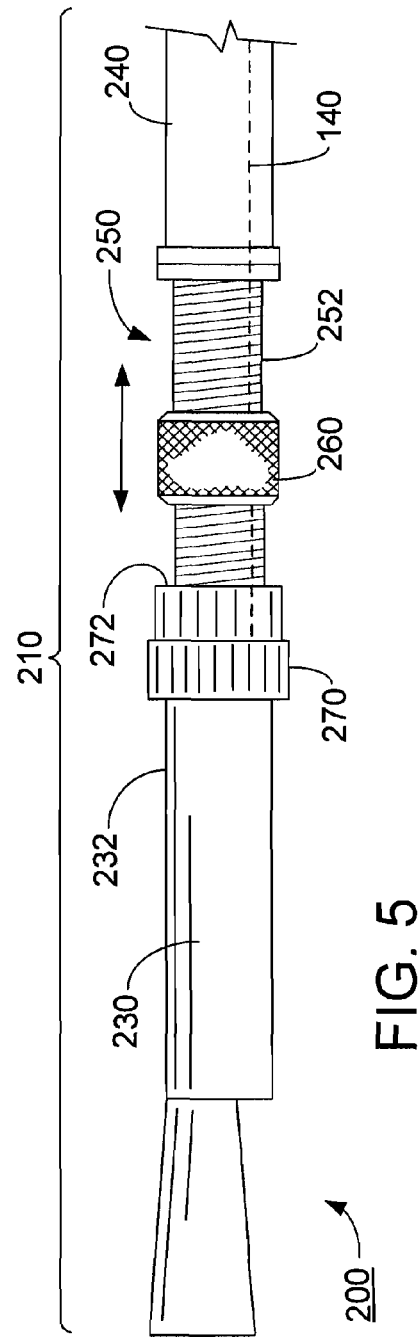
FIG. 5 is a side view of an implantable medical endoprosthesis delivery system.

FIG. 5 shows a proximal portion 210 of an implantable medical endoprosthesis delivery system 200. Proximal portion 210 includes a handle 230 and a tube 240 that are coupled to each other. Proximal portion 210 also includes a shaft 250 having a thread surface 252, a nut 260 and a member 270. One end of wire 140 is connected to member 270, and the opposite end of wire 140 is connected to a location at a distal portion of outer member 14 (not shown in FIG. 5).

Nut 260 and threaded surface 252 are configured so that nut 260 can be rotated on threaded surface 252 to move nut 260 in the proximal and distal directions. As nut 260 moves in the proximal direction, nut 260 eventually engages a surface 272 of member 270. Member 270 is configured to be able to slide along a surface 232 of handle 230 in the proximal and distal directions. Thus, when nut 260 is engaged with surface 272 of member 270, movement of nut 260 in the proximal direction results in corresponding movement of member 270 in the proximal direction.

With this arrangement, slack in wire 140 can be removed as follows. Nut 260 is rotated so that nut 260 moves in the proximal direction to engage surface 272 of member 270, and then nut 260 is further rotated to continue to move both nut 260 and member 270 in the proximal direction until the slack in wire 140 is removed. After removing the desired amount of slack in wire 140, outer member 14 can be refracted to expose stent 32 (not shown in FIG. 5) by moving member 270 in the proximal direction along surface 232. In some embodiments, it may be desirable to fix the relative positioning of nut 260 and member 270 relative to each other (e.g., to reduce the possibility of slack being re-introduced into wire 140). In certain embodiments, nut 260 can be fixed in place relative to member 270 by applying a suitable adhesive to nut 260 and/or threads 252. Examples of adhesives include cyanoacrylate adhesives, including medical grade cyanoacrylate adhesives, such as Loctite® brand products available from Henkel Technologies (e.g., Assure™ 425 Surface Curing Threadlocker).

The pitch of threads 252 can be selected to achieve a desired degree of control when removing the slack from wire 140. Generally, the finer the pitch of threads 252, the finer control an operator, e.g., a physician, has over the amount of slack removed per turn of nut 84. In some embodiments, threaded surface 252 can have a pitch of at least about 6.5 (e.g., at least about 13) turns per millimeter.

In general, shaft 250, nut 260 and member 270 are made of materials that compatible (e.g., so that rotation of nut 260 along surface 252 does not damage nut 260 or shaft 250, so that engagement of nut 260 with surface 252 does not damage nut 260 or member 270). In some embodiments, shaft 250, nut 260 and/or member 270 are made of plastic (e.g., nylon, polyester, polyethylene or polypropylene).

In some embodiments (e.g., when it is desired to enhance the ability of member 270 to slide along surfaces 252 of shaft 250), member 270 and/or shaft 250 can be formed of a material having a relatively low coefficient of friction (e.g., a fluoropolymer or a silicone), and/or member 130 and/or shaft 250 can be made of a material (e.g., a plastic) that includes a lubricious additive (e.g., a fluoropolymer, a silicone, an ultrahigh molecular weight polyethylene, an oil, or blends thereof). Examples of fluoropolymers include PTFE and FEP.

In general, stent 32 is a self-expanding stent. Examples of materials from which stent 32 can be include shape memory materials, such as nitinol, silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc/(Cu—Zn), copper-zinc-aluminum (Cu—Zn—Al), copper-zinc-tin (Cu—Zn—Sn), copper-zinc-xenon (Cu—Zn—Xe), iron beryllium (FesBe), iron platinum (FesPt), indium-thallium (In—Tl), iron-manganese (Fe—Mn), nickel-titanium-vanadium (Ni—Ti—V), iron-nickel-titanium-cobalt (Fe—Ni—Ti—Co) and copper-tin (Cu—Sn). For yet additional shape memory alloys, see, for example, Schetsky, L. McDonald, "Shape Memory Alloys", *Encyclopedia of Chemical Technology* (3rd ed.), John Wiley & Sons, 1982, vol. 20, pp. 726-736.

Inner member 12 and outer member 14 are generally made of polymeric materials. Examples of polymeric materials include polyether-block co-polyamide polymers (e.g., PEBAX®), copolyester elastomers (e.g., Arnitel® copolyester elastomers), thermoplastic polyester elastomers (e.g., Hytrel®), thermoplastic polyurethane elastomers (e.g., Pellethane™), polyeolefins (e.g., Marlex® polyethylene, Marlex® polypropylene), high-density polyethylene (HDPE), low-density polyethylene (LDPE), polyamides (e.g., Vestamid®), and combinations of these materials. In certain embodiments (e.g., when it is desirable to reduce the force used to retract outer member 14), outer member 14 and/or inner member 12 can be made of a material having a relatively low coefficient of friction (e.g., a fluoropolymer or a silicone).

Examples of fluoropolymers include PTFE and FEP. Alternatively or additionally, outer member 14 and/or inner member 12 can be made of a material that includes a lubricious additive (e.g., a fluoropolymer, a silicone, an ultrahigh molecular weight polyethylene, an oil, or blends thereof).

Wire 140 is typically made of a material having the appropriate level of strength and flexibility. Examples of materials from which wire 140 can be made include stainless steel, high modulus, oriented thermoplastic materials (e.g., fluoropolymers, nylons) and/or nitinol. Examples of fluoropolymers include PTFE and FEP.

While certain embodiments have been described, other embodiments are possible.

As an example, while embodiments have been described in which a set screw is used in the system, more generally any fastening device or mechanism can be used. For example, clamps can be used. Alternatively or additionally, crimping, snap fitting and/or adhesive materials can be used.

As another example, in certain embodiments, member 270 can have a threaded orifice/set screw arrangement as described above with respect to member 130. This can, for example, allow for additional flexibility and/or control in removing slack from wire 140.

As a further example, in some embodiments, an implantable medical endoprosthesis system can include a strain relief (e.g. located at a distal portion of the handle).

As an additional example, while embodiments have been described in which a stent is contained in the system, more generally the systems can contain any implantable medical endoprosthesis. Examples of implantable medical endoprosthesis include stent grafts and filters (e.g., arterial filters, venus filters).

As another example, while embodiments have been described in which a wire is present, more generally any device can be used that is capable coupling the adjustable stop with a portion (e.g., a distal portion) of outer member 14 so that, when there is substantially no slack in the device, as the device moves in the proximal direction the portion of outer member 14 also moves in the proximal direction. Examples of such devices include vascular coils (e.g., vascular coils designed for use for aneurysms).

Other embodiments are in the claims.

What is claimed is:

1. A medical endoprosthesis delivery system, comprising:
   an inner member;
   an outer member at least partially surrounding the inner member, the inner member and the outer member being configured so that an implantable medical endoprosthesis can be disposed therebetween;
   a coupling device coupled to a portion of the outer member so that, when there is substantially no slack in the coupling device, as the coupling device moves in a proximal direction the portion of the outer member moves in the proximal direction; and
   an adjustable stop releasably coupled to the coupling device so that, when there is slack in the coupling device, the adjustable stop can be released from the coupling device so that the amount of slack in the coupling device can be reduced by proximally retracting the coupling device relative to the adjustable stop;
   wherein the adjustable stop comprises:
      a handle region coupled to the inner member, the handle region including a first shaft having an outer surface and a second shaft having an outer surface disposed along a side surface of the outer surface of the first shaft with an opening therebetween, and
      a member that is moveable along the outer surface of the first shaft and the outer surface of the second shaft in the proximal direction,
      wherein the member includes an orifice configured to receive a fastening device.

2. The system of claim 1, further comprising the fastening device in the orifice of the member.

3. The system of claim 2, wherein the fastening device has a first position in which, as the member moves in the proximal direction along the outer surfaces of the first and second shafts respectively, the coupling device moves in the proximal direction, and a second position in which, as the member moves in the proximal direction along the outer surfaces of the first and second shafts respectively, the coupling device does not move in the proximal direction.

4. The system of claim 2, wherein the fastening device is a set screw.

5. The system of claim 2, wherein the fastening device comprises one or more elements selected from the group consisting of clamping devices, crimping devices, snap fitting devices and adhesive materials.

6. The system of claim 1, wherein the member is formed of multiple pieces of material.

7. A medical endoprosthesis delivery system, comprising:
   an inner member;
   an outer member at least partially surrounding the inner member, the inner member and the outer member being configured so that an implantable medical endoprosthesis can be disposed therebetween;
   a wire coupled to a portion of the outer member so that, when there is substantially no slack in the wire, as the wire moves in a proximal direction the portion of the outer member moves in the proximal direction; and
   an adjustable stop releasably coupled to the wire so that, when there is slack in the wire, the adjustable stop can be released from the wire so that the amount of slack in the wire can be reduced by proximally retracting the wire relative to the adjustable stop, the adjustable stop comprising:
      a first shaft coupled to the inner member and a second shaft arranged substantially parallel to the first shaft, the first shaft; and second shafts each having an outer surface with an opening therebetween; and
      a member that is moveable along the outer surface of the first shaft and the outer surface of the second shaft in the proximal direction, the member including an orifice; and
      a set screw in the orifice of the member, the set screw having a first position in which, as the member moves in the proximal direction along the outer surfaces of the first and second shafts respectively, the wire moves in the proximal direction, and a second position in which, as the member moves in the proximal direction along the outer surfaces of the first and second shafts respectively, the wire does not move in the proximal direction.

8. A stent delivery system, comprising:
   an inner member having a distal portion;
   a stent disposed about the distal portion of the inner member;
   an outer member disposed about the stent;
   a pull wire attached to the outer member and extending proximally therefrom to a handle;
   wherein the handle includes a first shaft having an outer surface, a second shaft having an outer surface and disposed along a side surface of the outer surface of the first shaft with an opening therebetween, and a member movable along the outer surface of the first shaft and the outer surface of the second shaft, the member having a groove formed therein;

wherein the pull wire is disposed in the groove;

wherein the member has an orifice formed therein; and a fastening device that is configured to be disposed in the orifice to releasably secure the member to the pull wire.

9. The stent delivery system of claim 8, wherein the orifice is threaded.

10. The stent delivery system of claim 8, wherein the fastening device includes a set screw.

11. The stent delivery system of claim 10, wherein when the set screw is disposed in the orifice, the set screw secures the pull wire to the member.

12. The stent delivery system of claim 10, wherein when the set screw is not disposed in the orifice, the pull wire is not secured to the member.

13. The stent delivery system of claim 10, wherein when there is slack present in the pull wire, the set screw can be positioned so that the pull wire is not secured to the member.

14. The stent delivery system of claim 13, wherein slack in the pull wire can be removed by pulling the pull wire in the proximal direction.

15. The stent delivery system of claim 14, wherein when any slack is removed from the pull wire, the set screw can be disposed in the orifice in a manner sufficient to secure the pull wire to the member.

16. The stent delivery system of claim 8, wherein pulling the pull wire proximally moves the outer member proximally.

17. The stent delivery system of claim 8, wherein the stent is a self-expanding stent.

\* \* \* \* \*